United States Patent [19]
Butler et al.

[11] Patent Number: 5,138,163
[45] Date of Patent: Aug. 11, 1992

[54] DIRECT SAMPLING OF ENGINE EMISSIONS FOR INSTANTANEOUS ANALYSIS

[75] Inventors: James W. Butler, Dearborn Heights; Alex D. Colvin, Oak Park; Thomas J. Korniski, Livonia, all of Mich.

[73] Assignee: Ford Motor Company, Dearborn, Mich.

[21] Appl. No.: 756,701

[22] Filed: Sep. 9, 1991

[51] Int. Cl.$^5$ .................... G01M 15/00; G01N 21/37
[52] U.S. Cl. .................... 250/339; 250/341; 250/343; 73/116; 73/117.3
[58] Field of Search ............... 356/439; 73/1 G, 116, 73/117.2, 117.3; 250/338.5, 339, 340, 341, 343

[56] References Cited

U.S. PATENT DOCUMENTS

| | | | |
|---|---|---|---|
| 4,389,881 | 6/1983 | Butler et al. | 73/116 |
| 4,586,367 | 5/1986 | Lewis | 73/116 X |
| 4,727,746 | 3/1988 | Mikasa et al. | 73/116 X |
| 4,801,805 | 1/1989 | Butler | 250/343 |
| 4,928,015 | 5/1990 | Butler et al. | |

FOREIGN PATENT DOCUMENTS 63-148148  6/1988  Japan .................... 356/439

*Primary Examiner*—Constantine Hannaher
*Assistant Examiner*—Edward J. Glick
*Attorney, Agent, or Firm*—Joseph W. Malleck; Roger L. May

[57] ABSTRACT

A method and associated apparatus for on-line gas analysis of a multicomponent gas emission flow, comprising: continuously withdrawing and regulating the pressure of a first sample flow from the emission flow, continuously withdrawing a second sample flow from the first sample flow, the second flow sample being diluted with mass controlled amounts of diluent ($N_2$ or air) to lower the dew point of the gas sample to below room temperature; controlling the absolute pressure of the diluted sample to the range of 920–950 mbar; frequently periodically analyzing the diluted sample flow, controlled as to pressure, by fourier-transform infrared spectrometric techniques to render a concentration measurement for each desired gas species; and correcting each concentration measurement for dilution to derive an undiluted concentration measurement representative of the actual exhaust gas, said correction being accomplished by measuring the actual air/fuel ratio of the gas emission flow to provide a theoretical carbon concentration in the undiluted exhaust gas and thereafter ratioing the theoretical total carbon concentration to the measured carbon concentration in the sample to provide the needed correction factor.

17 Claims, 3 Drawing Sheets

```
┌─────────────────────────────────────────┐
│ WITHDRAW AND REGULATE A FIRST SAMPLE STREAM │
│        TO A PREDETERMINED PRESSURE          │
└─────────────────────────────────────────┘
                    │
                    ▼
┌─────────────────────────────────────────┐
│    WITHDRAW A SECOND SAMPLE FLOW        │
│  FROM THE FIRST STREAM AND ACCURATELY   │
│    DILUTE SECOND SAMPLE FLOW TO         │
│         LOWER ITS DEW POINT             │
└─────────────────────────────────────────┘
                    │
                    ▼
┌─────────────────────────────────────────┐
│     CONTROL ABSOLUTE PRESSURE OF        │
│  DILUTED SAMPLE FLOW TO 920-950 mbar    │
└─────────────────────────────────────────┘
                    │
                    ▼
┌─────────────────────────────────────────┐
│   SUBJECT DILUTED SAMPLE FLOW TO FTIR   │
│   SPECTROMETRIC ANALYSIS TO PROVIDE     │
│     A CONCENTRATION FOR EACH SPECIES    │
└─────────────────────────────────────────┘
                    │
                    ▼
┌─────────────────────────────────────────┐
│   CORRECT CONCENTRATION ANALYSIS FOR    │
│   DILUTION USING A RATIO OF ACTUAL      │
│    AND THEORETICAL CARBON IN FLOW       │
└─────────────────────────────────────────┘
```

Fig. 1

DIRECT SAMPLING OF ENGINE EMISSIONS FOR INSTANTANEOUS ANALYSIS

BACKGROUND OF THE INVENTION

1. Technical Field

This invention relates to the art of gas analysis, and more particularly to techniques for on-line analysis of hot exhaust emissions from engines.

2. Description of the Prior Art

Until very recently, on-line gas analysis of engine exhaust emissions has not been attempted because instantaneous on-line analysis appeared impossible. Prior art gas analysis techniques usually included chemiluminescence, flame ionization, and total hydrocarbon analysis, or analysis by the use of solids or liquids off-line from the flow of gases. These modes have proven inadequate because: (a) the analysis is usually of a single component; (b) takes too long, sometimes weeks; (c) the data for separate components has no commonality in response time and thus cannot be readily combined; (d) the sensed data suffers from cross-interferences of the added chemicals; and (e) some gaseous components cannot be analyzed.

Recently, infrared spectroscopy has been transferred from a quality control technique to a gas analysis technique in U.S. Pat. No. 4,928,015. This first initial application of fourier-transform, infrared spectrometric techniques to engine emission analysis required the use of constant volume sampling of the gas stream coupled with dilution of the gas flow to eliminate the problem of high water content of the exhaust. The sample is diluted to lower the dew point of the sample. This avoids the necessity of keeping the entire stream very hot at great difficulty, or of removing the water from the sample, which is even more difficult, without risking loss of some components and thus upsetting the accuracy of the measurements. This particular patent, although advancing the art significantly, does not provide for the direct measurement of mass emission rates because the technique does not require the exhaust mass flow.

An object of this invention is to provide a feature, not achievable by the prior art, which includes instantaneously sampling a fraction of the exhaust without either heating or condensing water for the direct on-line measurement of engine exhaust emissions.

SUMMARY OF THE INVENTION

This invention, in a first aspect, is an improved method of on-line gas analysis of a multicomponent gas emission flow. Such method essentially comprises: (a) continuously withdrawing a first sample flow from the gas emission flow and regulating the first sample flow pressure; (b) withdrawing a second sample flow from the regulated sample flow, the second sample flow being diluted with mass controlled amounts of diluent to lower the dew point of the second sample flow to below room temperature; (c) controlling the absolute pressure of the diluted sample to the range of 920–950 mbar; (d) frequently periodically analyzing the diluted sample flow, controlled as to pressure, by fourier-transform infrared spectrometric techniques to render a concentration measurement for each desired gas species; and (e) correcting each concentration measurement for dilution to derive an undiluted concentration measurement representative of the actual exhaust gas, said correction being accomplished by measuring the actual air/fuel ratio of the gas emission flow to provide a theoretical carbon concentration in the undiluted exhaust gas and thereafter ratioing the theoretical total carbon concentration to the measured carbon concentration in the sample to provide the needed correction factor.

Preferably, the withdrawal step is carried out by the use of a vacuum pump if the sample is below atmospheric pressure, or without the use of a pump if the sample pressure is greater than 1 inch Hg (pig). If the pump is used, it is disposed downstream of the analysis location and adapted to provide a regulated withdrawal pressure of about 0.5 inch Hg. The diluent is nitrogen or air introduced at room temperature, regulated to a mass flow of about 30 L/min. The pressure in the analysis stream is controlled by comparing a sensed pressure of the emission flow with a desired reference pressure signal and using the difference therebetween as an indicator to adjust the flow to achieve the desired pressure.

The second aspect of this invention is an apparatus for carrying out on-line gas analysis of a multicomponent gas emission flow. The apparatus comprises: (a) means for withdrawing a first sample flow from the gas emission flow and regulating the first sample flow pressure, and for withdrawing a second sample flow from the first regulated sample flow, the second sample flow being diluted with mass controlled amounts of diluent to lower the dew point of the second sample flow to below room temperature; (b) means for controlling the pressure of the diluted sample flow to a level below 950 mbar; (c) an FTIR spectrometric device for measuring the concentration for each desired gas species within the emission flow; and (d) means for correcting the concentration measurement for dilution to derive an undiluted concentration measurement representative of the actual exhaust emission, the correction being accomplished by use of means for measuring the actual air/fuel ratio to provide a theoretical carbon concentration in undiluted exhaust gas and thereafter ratioing the theoretical total carbon content to the measured carbon content for the species sample to provide the needed correction factor.

Preferably, the means of generating a pressure regulated first sample flow comprises a pressure regulator operating with the aid of a pump if the sample flow is below 1 inch Hg pressure, or without the aid of a pump if the first sample flow pressure is greater than 1 inch Hg pressure.

Preferably, the means for withdrawing the second sample flow from the first regulated flow, comprises a sampling tube having an internal diameter in the range of 0.06–0.09 inches and 4–6 inches long. The diluent is introduced from a source of nitrogen or air; the diluent is controlled by a mass flow controller. The means for withdrawal may further comprise a particulate filter and/or a back pressure valve for control of the first sample flow (undiluted exhaust pressure).

The means for controlling the pressure preferably comprises an absolute pressure gauge having a microswitch and a valve control circuit, which circuit effects the operation of a flow controller.

The means for correcting the concentration measurement comprises an air/fuel analyzer interposed in a capillary flow of the gas emission and which analyzer is electronically connected with a computer for making the mathematical carbon ratio calculations and eventual correction.

BRIEF DESCRIPTION OF THE DRAWINGS

FIG. 1 is a flow diagram depicting the steps of the process of this invention;

DETAILED DESCRIPTION AND BEST MODE METHOD ASPECTS

Figure 2:
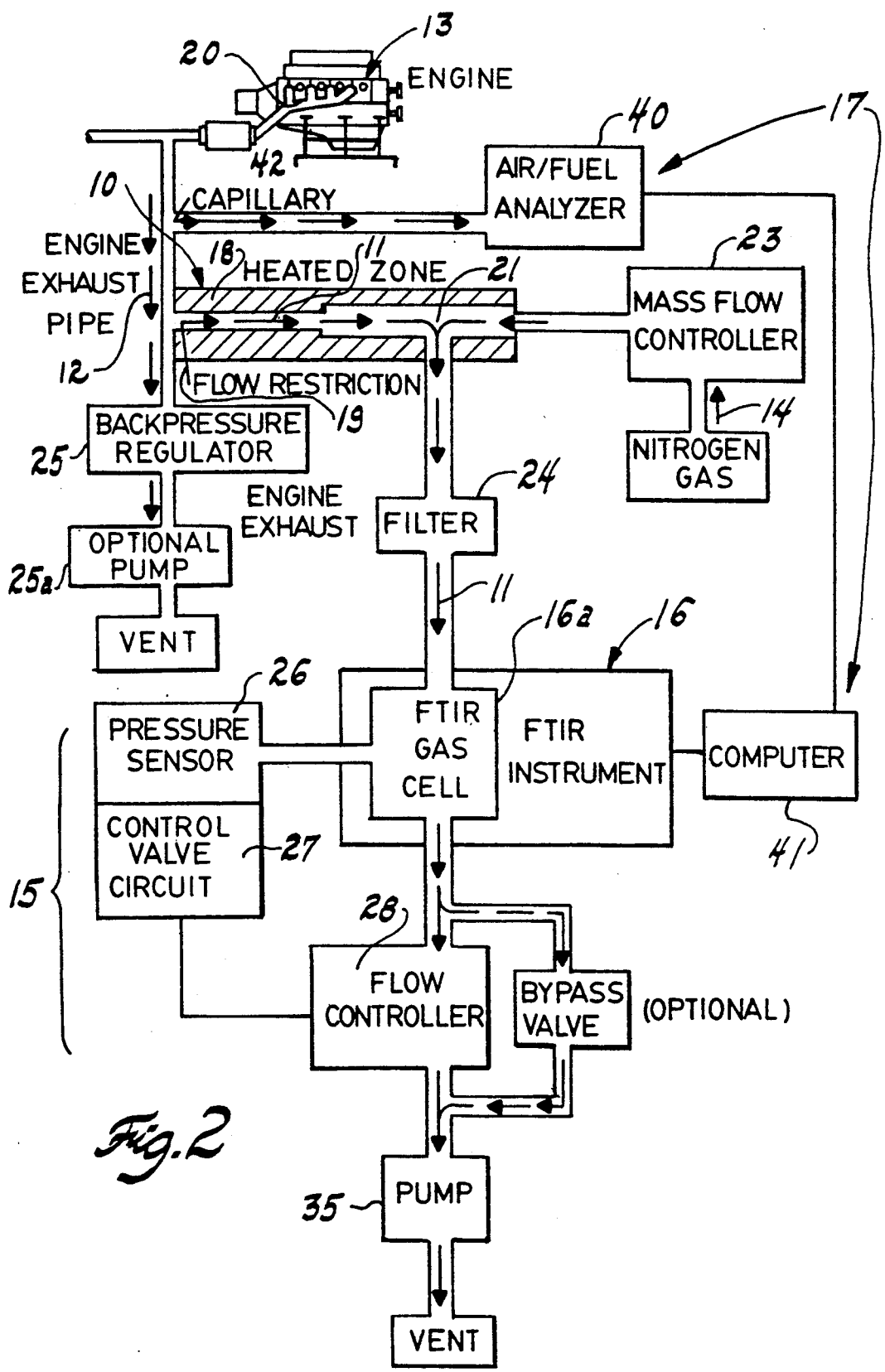
FIG. 2 is a block diagram of the apparatus for this invention.

As shown in FIG. 1, the process steps essentially comprise withdrawing a first sample flow from engine exhaust and controlling such sample flow to a predetermined pressure, withdrawing a second sample flow from the first sample flow but diluted and independently controlled as to temperature and pressure, analyzing the second sample flow by FTIR techniques to generate a concentration for each gas species, and accurately and simply correcting the concentration for dilution effect.

Withdrawing a pressure regulated first sample flow is effected by sequestering a flowing sample through a passage that extracts about 5–8% of the exhaust volume, the first flow being mechanically regulated. The sequestration of a small second flow is through a narrow tube which extracts <5% of the exhaust volume flow, assuming the inlet pressure to the tube is in the range of −0.2/+1 Hg. Dilution gas is fed into the narrow tube under which it is independently controlled to a pressure of about 920–950 mbar (preferably 933) and at a steady mass flow (such as about 30 L/min) to avoid chemical noise in the subsequent analysis step. The portion of sample extraction system and the tubes that retain the emission flow, prior to dilution, should be protected so as to prevent water condensation; this may be effected by use of insulation or very light heating to maintain a high temperature within the exhaust gas at least above 165° F. Practically, the temperature should be reduced sufficiently to about 75° F. so that the dew point temperature will be in the range of about 64°–68° F. The pressure of the sample flow is desirably controlled to about 700 mm Hg (933 mbar), this pressure is desirable to attain in order to make direct comparison with the reference spectra previously determined by FTIR at a pressure also at about 700 mm Hg.

Analysis of the sample gas flow is provided by use of FTIR spectrometric techniques such as disclosed in U.S. Pat. No. 4,928,015, the disclosure of which is incorporated herein by reference.

Correction is effected by establishing the dilution factor. This dilution factor is derived from the ratio of the expected total carbon concentration and the measured total carbon concentration in the diluted sample. The expected total carbon concentration is a function of the fuel type and the air/fuel ratio of the engine. The air/fuel ratio can be measured continuously with a simple air/fuel analyzer, such as described in U.S. Pat. No. 4,389,881, the disclosure of which is incorporated herein by reference, and the theoretical total carbon concentration is calculated. Since the FTIR simultaneously measures the concentration of $CO_2$, CO, and hydrocarbons, the total carbon concentration of the diluted sample is readily available on a substantially instantaneous basis. The measured total carbon concentration is then compared to the theoretical total carbon and the dilution factor calculated. The calculation allows the determination of the effective dilution factor based on measured air/fuel ratio.

More specifically, the dilution factor is calculated as follows. An air/fuel analyzer will supply an analog output proportional to the oxygen fraction in the exhaust gas. This signal is digitized for each sample and lambda ($\lambda$) is calculated as follows:

lean case, $$\lambda = \frac{1 + F\left(\frac{N + 2P}{4 + N - 2P}\right)}{1 - F\left(\frac{0.79}{0.21}\right)},$$

rich case, $$\lambda = \frac{1 + F\frac{(4 + 2N - 2P)}{(4 + N - 2P)}}{1 - F\left(\frac{0.79}{0.21}\right)}.$$

Where F is the oxygen fraction, N the hydrogen carbon ratio, and P the oxygen carbon ratio. Once $\lambda$ is determined, the inverse carbon concentration (the ratio of moles of exhaust to moles of carbon) can be calculated as follows:

lean case, (4)

$$(C_{Theo})^{-1} = \frac{\lambda}{0.21}\left(1 + \frac{N}{4} - \frac{P}{2}\right) + \frac{N}{4} + \frac{P}{2} + \frac{2}{3}X + 0.535Y,$$

rich case, $$(C_{Theo})^{-1} = 1 + \frac{N}{2} + \lambda\left(\frac{0.79}{0.21}\right)\left(1 + \frac{N}{4} - \frac{P}{2}\right) - 0.93Y.$$

With X the number of moles of CO, and Y the number of moles of $CH_{1.86}$.

The dilution factor is determined using:

$$D = \frac{1}{(C_{Theo})^{-1} \times C_{Meas}}.$$

Where $C_{meas}$ is the total carbon measured. This factor is then applied to all the concentrations measured.

Usually, D is first approximated by calculating $(C_{theo})^{-1}$ when setting X and Y to zero. The approximate dilution factor is then applied to the CO and hydrocarbon concentrations and $(C_{theo})^{-1}$ is recalculated along with the dilution factor. This corrected dilution factor is used in the final calculations. The correction for hydrocarbon contribution may be small. For example: for M85 fuel (N=3.406, P=0.724) and $\lambda=1$, evaluating equation 4 with Y=0 (i.e., no hydrocarbon) gives $(C_{theo})^{-1}=8.306$. If the total hydrocarbon concentration is 5000 ppm, then 0.93 Y is 0.0047. Therefore, neglecting the hydrocarbon contribution in this case introduces a 0.06% error.

APPARATUS

The improved apparatus of this invention provides an on-line gas analysis of a multicomponent gaseous emission. As shown in FIG. 2, the apparatus comprises essentially: means 10 for withdrawing a first sample flow 12 from engine emission flow 9 emitted by an internal combustion engine 13 and a second sample flow 11 from the first sample flow, the second sample flow 11 being diluted with a mass control diluent 14 to lower the dew point of the second sample flow to below room temperature; means 15 for controlling the absolute pressure of the diluted second sample flow to the range of 920–950 mbar; an FTIR spectrometric device 16 for measuring the concentration of each gas species in such second sample gas flow 11; and means 17 for correcting the concentration measurement for dilution to derive an undiluted concentration measurement representative of the actual exhaust gas.

The means 10 for withdrawing includes a sampling tube 18 which may have a 0.06–0.09 (preferably 0.07) inch internal diameter and 4–6 (preferably 5) inch length. Such capillary tube 18 may be mounted with silver solder into a stainless steel tube (not shown) that is inserted into the exhaust pipe. The sampling tube 18 has a narrower inlet portion at 19 and is insulated or provided with minimal heating, depending on the distance from the engine exhaust manifold 20 and the exhaust gas temperature. The minimum heating requirements also apply to any additional sampling system components upstream of the sampling tube through and including the diluent gas mixing zone 21 described below. The sample flow is diluted by use of the pressurized diluent gas 14 which is mixed and blended within the sample flow tube in zone 21 (preferably within the portion containing a tee) at a rate of about 30 L/min. The diluent is a gas of dry nitrogen or air controlled as to flow by a mass flow controller 23. The diluent gas 14 should be a continuous, steady flow to reduce noise in the analysis and thus the need for use of a mass flow controller. The dilution of the exhaust gas maintains all the exhaust components in the gas phase at room temperature and therefore no condensation occurs nor is any further heating required downstream of the dilution point. The diluted second sample flow may preferably be filtered by use of a filter membrane 24 (such as 142 mm Pallflex-type 2500QA0 tissuequartz membrane with backing) contained in a stainless steel holder at room temperature. After filtering, the sample flow may be passed to the FTIR device 16.

Adjacent the inlet to the second sample flow 11, a back pressure regulator 25 may be deployed to control the pressure in the first sampling flow 12. Such pressure control may range from −0.2 to +1 inches of mercury. The optimum back pressure for the initial test is about 0.5 inches of mercury. 0.5 inches of mercury back pressure did provide an 8.4:1 dilution ratio of the exhaust at the 30 L/min dilution flow and an FTIR sample dew point of about 64° F. That condition allowed eight hours of continuous FTIR sampling. However, with one inch of mercury back pressure, a 7.2:1 dilution ratio at 30 L/min dilution flow will result, providing a 68° F. sample dew point. Too high of an engine exhaust back pressure causes insufficient dilution of the exhaust and possible condensation in the FTIR device, which may damage its optical cell and generate inaccurate test results. The effects of excessive exhaust back pressure is offset by the back pressure regulator 25 so that a wide range of engine pressures can be accommodated.

Figure 3:
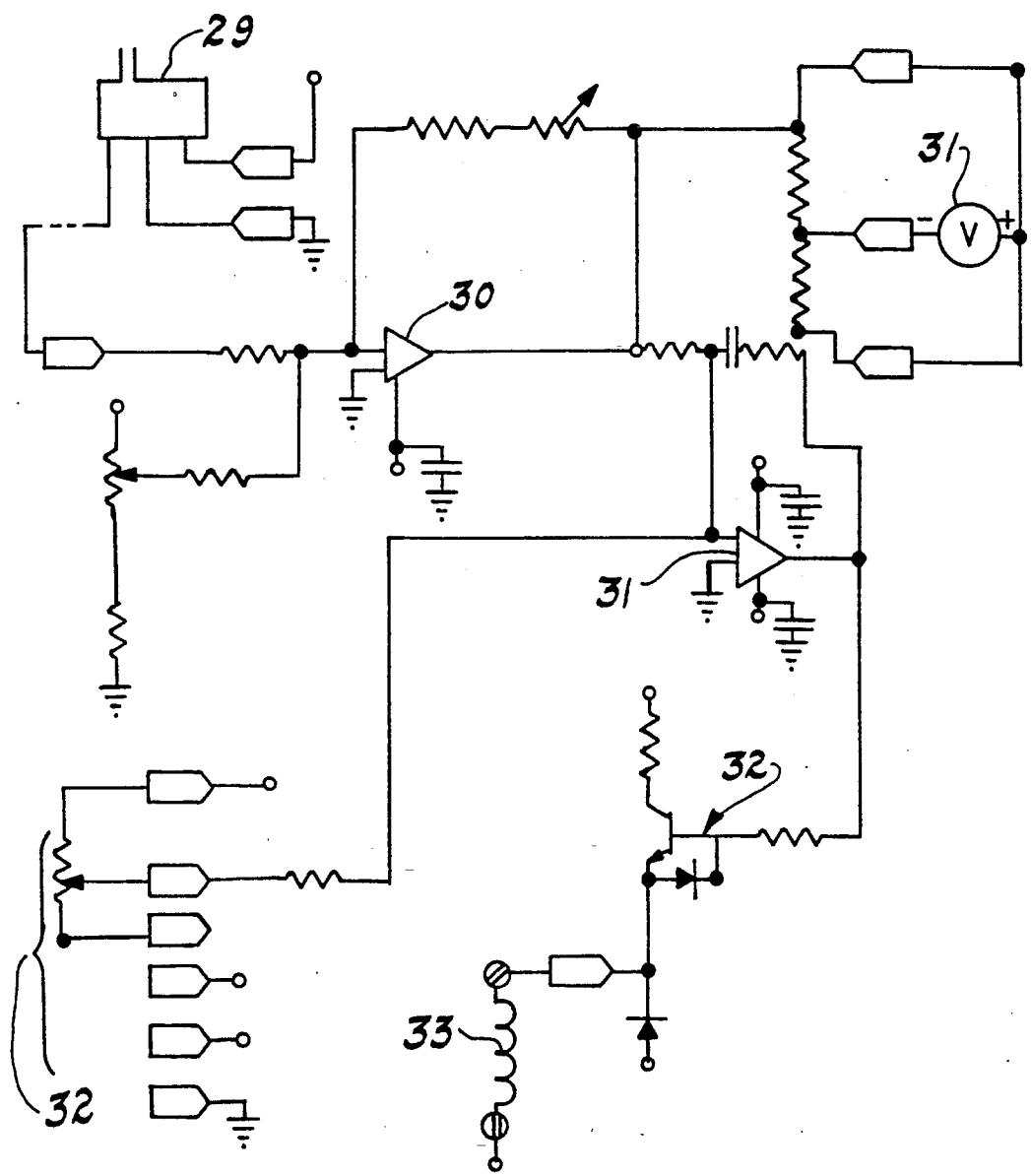
FIG. 3 is a schematic circuit diagram useful for sensing and controlling the absolute pressure of the sample emission flow.

The means 15 for controlling the pressure of the diluted second sample flow comprises a pressure sensor 26 and a control valve circuit 27 which uses the signal for the pressure sensor to operate a flow controller 28. The control valve circuit 26 is shown more illustratively in FIG. 3. It is used to control the absolute pressure of the diluted sample for the FTIR device. The pressure, as measured by an absolute pressure gauge 29 or sensor, is compared with a reference signal corresponding to the desired pressure. The absolute pressure gauge 29, and its output is offset and multiplied by an amplifier 30 so that the output of the amplifier is about 0.01 volt/millibar. The pressure signal from the amplifier 30 is divided by 10 and displayed on a digital volt meter 31. A reference signal from a signal generator 32 is set equal and opposite in polarity to the pressure signal from the amplifier 30 at the null condition. Then, a second amplifier 31 is used as an augmented integrator to drive a transistor 32, powering the coil 33 of the controller 28. The linear control valve of the controller 28 is located between the FTIR cell 16 and a vacuum pump 35. The valve of the controller 28 is controlled by circuit 27 to keep the detected pressure in the FTIR cell 16a at a predetermined value, such as 933 millibars. Thus, the pressure, as measured by the absolute pressure gauge, is compared with a reference signal corresponding to the desired pressure. A conventional feedback control amplifier 31 provides the valve control signal based on the difference between the pressure signal and the desired reference signal. Thereby, the valve controller regulates the sample flow to the vacuum pump 35 to achieve the desired sample pressure.

Analyzation is carried out by the use of an FTIR device such as disclosed in U.S. Pat. No. 4,928,015.

The means 17 for correcting the concentration measurements comprises an air/fuel analyzer 40 and a computer 41. The dilution factor is established from the ratio of the expected total carbon concentration and the measured total carbon concentration in the diluted sample. The expected total carbon concentration is a function of the fuel type in the air/fuel ratio of the engine. The air/fuel ratio is measured continuously by the use of the air/fuel analyzer 40 which draws a sample flow from the main gas emission flow through a capillary 42. The theoretical carbon concentration is calculated (in accordance with the steps explained under Method) by use of the computer and by using simultaneous FTIR measurements for $CO_2$, CO, and hydrocarbons. The total carbon concentration of the diluted sample will then be readily available on a three-second basis. The measured total carbon concentration is compared to the theoretical total carbon and the dilution factor calculated. The calculation allows determination of the effective dilution factor based on measured air/fuel ratio.

While particular embodiments of the invention have been illustrated and described, it will be obvious to those skilled in the art that various changes and modifications may be made without departing from the invention, and it is intended to cover in the appended claims all such modifications and equivalents as fall within the true spirit and scope of this invention.

We claim:

1. A method of on-line gas analysis of a multicomponent gas emission flow comprising gas species, comprising:

(a) continuously withdrawing a first sample flow from said gas emission flow and regulating the first sample flow pressure:

(b) continuously withdrawing a second sample flow from said first sample flow, said second sample flow being diluted with mass controlled amounts of diluent to lower the dew point of the second sample flow to below room temperature;

(c) controlling the absolute pressure of said diluted second sample to the range of 920–950 mbar;

(d) frequently periodically analyzing the diluted second sample flow, controlled as to pressure, by fourier-transform infrared spectrometric techniques to render a concentration measure for one or more of said gas species and carbon in such species; and (e) correcting said one or more concentration measures for dilution to derive an undiluted concentration measure, said correction being accomplished by measuring the actual air/fuel ratio used to provide the gas emission flow, such actual A/F measurement being used to provide a theoretical carbon concentration for each said undiluted concentration measure and thereafter ratioing said theoretical carbon concentration to said carbon concentration measure for said ne or more gas species to provide a correction factor.

2. The method as in claim 1, in which withdrawal of step (a) is carried out by use of a vacuum pump disposed downstream of the first sample flow and inlet to the second sample flow.

3. The method as in claim 2, in which said vacuum pump promotes a withdrawal pressure of 0.4–1.0 inch Hg pressure.

4. The method as in claim 1, in which said diluent of step (b) is dry nitrogen or air introduced at or about room temperature.

5. The method as in claim 1, in which the introduction of diluent in step (b) to the sample flow is regulated to a mass flow of about 30 L/min.

6. The method as in claim 1, in which in step (c) the absolute pressure is controlled by comparing a sensed pressure with a desired reference signal and then using the difference as an indicator to adjust flow to achieve the desired absolute pressure.

7. The method as in claim 6, in which said absolute pressure of said diluted second sample flow is controlled within the tolerance of ±0.1%.

8. The method as in claim 1, in which said absolute pressure of said diluted second sample flow is regulated electronically.

9. The method as in claim 8, in which said electronic regulation is carried out by use of an electronic pressure sensor to measure the absolute pressure of the sample flow, a signal of said sensor being amplified and set equal and opposite to a reference pressure signal at the null, the difference of said pressure signals being used to drive a transistor and coil and thence a flow controller.

10. The method as in claim 1, in which the second sample flow is diluted to a ratio of about 10:1.

11. The method as in claim 1, in which said gas emission flow is from internal combustion of a fossil fueled engine having an air/fuel controller, and in step (e) the air/fuel is measured by an analyzer having a lambda accuracy of 35 0.003.

12. The method as in claim 1, in which the pressure of said diluted sample is controlled to about 933 mbar.

13. An improved method for on-line gas analysis of a multicomponent gas emission flow, comprising:

(a) means for withdrawing by suction a sample flow from the emission flow emitted by an internal combustion engine, the sample flow being diluted with a mass controlled diluent to lower the dew point of the gas sample to below room temperature;

(b) means for controlling the pressure of the diluted sample flow to a level of about 933 mbar;

(c) FTIR spectrometric device for measuring the concentration for each desired gas species within said diluted sample flow; and means for correcting the concentration measure to derive an undiluted concentration measure, such correction being accomplished by measuring the actual air/fuel ratio used to provide the gas emission flow, such actual A/F ratio being used to provide a theoretical carbon concentration for each undiluted concentration measure and thereafter ratioing said theoretical total carbon concentration to said carbon concentration measure for each gas species to provide a correction factor for such each gas species.

14. The apparatus as in claim 13, in which said means for withdrawing comprises a sampling tube, a source of pressurized diluent, and a mass flow controller for introducing the diluent to the sample tube.

15. The apparatus as in claim 14, comprising, further, a filter for extracting particulates from said gas flow prior to entering the FTIR device.

16. The apparatus as in claim 13, in which said means for controlling the pressure comprises an absolute pressure sensor, a valve responsive to the signal from said pressure sensor, and a flow controller responsive to said valve.

17. The apparatus as in claim 13, in which said means for correcting comprises an air/fuel analyzer for measuring the air/fuel ratio accurately, and a computer for comparing measurements of said FTIR spectrometric device with the air/fuel ratio measurement to achieve said correction factor.

* * * * *